United States Patent
Chang

(10) Patent No.: US 7,083,935 B2
(45) Date of Patent: Aug. 1, 2006

(54) ANDROGEN RECEPTOR COMPLEX-ASSOCIATED PROTEIN

(75) Inventor: Tai-Jay Chang, Taipei (TW)

(73) Assignee: Veterans General Hospital (TW)

( * ) Notice: Subject to any disclaimer, the term of this patent is extended or adjusted under 35 U.S.C. 154(b) by 0 days.

(21) Appl. No.: 11/189,521

(22) Filed: Jul. 26, 2005

(65) Prior Publication Data

US 2005/0272099 A1    Dec. 8, 2005

Related U.S. Application Data

(63) Continuation of application No. 09/781,693, filed on Feb. 12, 2001.

(60) Provisional application No. 60/262,312, filed on Jan. 17, 2001.

(51) Int. Cl.
*G01N 33/53* (2006.01)
*C07K 14/00* (2006.01)

(52) U.S. Cl. .................. 435/7.2; 435/69.1; 530/350

(58) Field of Classification Search ............... None
See application file for complete search history.

(56) References Cited

FOREIGN PATENT DOCUMENTS

| EP | 1106690 A | 6/2001 |
|----|-----------|--------|
| WO | WO 97/44490 | 11/1997 |
| WO | WO22/04152 | 1/2000 |
| WO | WO 01/07471 | 2/2001 |
| WO | WO 01/53315 | 7/2001 |

OTHER PUBLICATIONS

Decision by the Prime Minister: "Goal of Project". Regarding Millennium Project (New Millennium Project). pp. 58 and 62, Dec. 19, 1999 (with English Abstract.).

R. W. Ould (translated by Motoaki Anai). Principle of Genetic Engineering, 3$^{rd}$ Edition, pp. 115, lines 15-20, Apr. 20, 1997 (with English Abstract.).

Miyamoto, et al. *Promotion of agonist activity of antiandrogens by the androgen receptor coactivator, ARA70, in human prostate cancer DU145 cells.* Proc. Natl. Acad. Sci. 95:7379-7384, Jun. 1998.

Moilanen, et al. *Identification of a novel RING finger protein as a coregulator in steroid receptor-mediated gene transcription.* Molecular and Cellular Biology 18(9):5128-5139, 1998.

Akira, et al. *Protein inhibitor of activatored STAT3 regulated androgen receptor singaling in prostate carcinoma cells.* Biochemical and Biophysical Research Comunications 278(1):9-13, Nov. 2000.

Kang, et al. *Cloning and characterization of human prostate coactivator ARA54, a novel protein that associates with the androgen receptor.* Journal of Biological Chemistry 274(13):8570-8576, Mar. 1999.

Miguel Beato, "Gene Regulation by Steroid Hormones", Feb. 10, 1989, Cell, vol. 56;335-344.

Chen et al., "Nuclear Receptor Coactivator ACTR Is a Novel Histone Acetyltransferase and Forms a Multimeric Activation Complex with P/CAF and CBP/p300", Aug. 8, 1997, Cell, vol. 90;569-580.

Lui et al., "Analysis of Glucocorticoid Receptors in Human Hepatocellular Carcinoma and HepG2 cells", Nov. 4, 1993, Hepatology, vol. 18;1167-1174.

Bert O'Malley, "The Steriod Receptor Superfamily: More Excitement Predicted for the Future", Mol Endo, vol. 4 No. 3;363-369.

*Primary Examiner*—Michael Pak
(74) *Attorney, Agent, or Firm*—Fish & Richardson P.C.

(57) ABSTRACT

The invention relates to new proteins that bind to and aide the transactivation activity of androgen receptors, and nucleic acids encoding them.

9 Claims, No Drawings

ANDROGEN RECEPTOR COMPLEX-ASSOCIATED PROTEIN

CROSS-REFERENCE TO RELATED APPLICATIONS

This application is a continuation application of U.S. application Ser. No. 09/781,693, filed Feb. 12, 2001 and now pending and allowed, which claims priority from U.S. Provisional Application No. 60/262,312, filed Jan. 17, 2001. The contents of the two parent applications are incorporated by reference in their entirety.

BACKGROUND OF THE INVENTION

A variety of genes that are overexpressed in tumor cells relative to healthy cells have been identified. It is expected that the identification of such genes will provide drug targets for anti-cancer drug development and for cancer diagnostics. The number of steroid receptors (e.g., androgen receptors) in liver tumors cells appears to be increased relative to their adjacent healthy liver cells.

Steroid hormones generally exert their physiological effects by binding to their specific nuclear receptors to form complexes that in turn act as transcription factors. The complexes bind to specific nucleotide sequences (steroid responsive elements) in the promoters of steroid-responsive genes to facilitate transcription of those genes.

SUMMARY OF THE INVENTION

The invention is based on the discovery of a human protein that is overexpressed in hepatoma cells relative to normal adjacent tissue in liver cancer patients. It was also discovered that this human protein binds to an androgen receptor and moreover augments the ability of the androgen receptor to transactivate an androgen-responsive gene. Thus, the human protein to which this invention pertains was designated androgen receptor complex-associated protein or ARCAP. The full-length human ARCAP cDNA, with the start and stop codons underlined, is shown below.

(SEQ ID NO:3)
CCGGCTCAGGCAGAGCC<u>ATG</u>TCTCGGGGTGGCTCCTACCCACACCTGTTG

TGGGACGTGAGGAAAAGGTCCCTCGGGCTGGAGGACCCGTCCCGGCTGCG

GAGTCGCTACCTGGGAAGAAGAGAATTTATCCAAAGATTAAAACTTGAAG

CAACCCTTAATGTGCATGATGGTTGTGTTAATACAATCTGTTGGAATGAC

ACTGGAGAATATATTTTATCTGGCTCAGATGACACCAAATTAGTAATTAG

TAATCCTTACAGCAGAAAGGTTTTGACAACAATTCGTTCAGGGCACCGAG

CAAACATATTTAGTGCAAAGTTCTTACCTTGTACAAATGATAAACAGATT

GTATCCTGCTCTGGAGATGGAGTAATATTTTATACCAACGTTGAGCAAGA

TGCAGAAACCAACAGACAATGCCAATTTACGTGTCATTATGGAACTACTT

ATGAGATTATGACTGTACCCAATGACCCTTACACTTTTCTCTCTTGTGGT

GAAGATGGAACTGTTAGGTGGTTTGATACACGCATCAAAACTAGCTGCAC

AAAAGAAGATTGTAAAGATGATATTTTAATTAACTGTCGACGTGCTGCCA

CGTCTGTTGCTATTTGCCCACCAATACCATATTACCTTGCTGTTGGTTGT

TCTGACAGCTCAGTACGAATATATGATCGGCGAATGCTGGGCACAAGAGC

TACAGGGAATTATGCAGGTCGAGGGACTACTGGAATGGTTGCCCGTTTTA

TTCCTTCCCATCTTAATAATAAGTCCTGCAGAGTGACATCTCTGTGTTAC

AGTGAAGATGGTCAAGAGATTCTCGTTAGTTACTCTTCAGATTACATATA

TCTTTTTGACCCGAAAGATGATACAGCACGAGAACTTAAAACTCCTTCTG

CGGAAGAGAGAAGAGAAGAGTTGCGACAACCACCAGTTAAGCGTTTGAGA

CTTCGTGGTGATTGGTCAGATACTGGACCCAGAGCAAGGCCGGAGAGTGA

ACGAGAACGAGATGGAGAGCAGAGTCCCAATGTGTCATTGATGCAGAGAA

TGTCTGATATGTTATCAAGATGGTTTGAAGAAGCAAGTGAGGTTGCACAA

AGCAATAGAGGACGAGGAAGATCTCGACCCAGAGGTGGAACAAGTCAATC

AGATATTTCAACTCTTCCTACGGTCCCATCAAGTCCTGATTTGGAAGTGA

GTGAAACTGCAATGGAAGTAGATACTCCAGCTGAACAATTTCTTCAGCCT

TCTACATCCTCTACAATGTCAGCTCAGGCTCATTCGACATCATCTCCCAC

AGAAAGCCCTCATTCTACTCCTTTGCTATCTTCTCCAGACAGTGAACAAA

GGCAGTCTGTTGAGGCATCTGGACACCACACACATCATCAGTCTGATAAC

AATAATGAAAAGCTGAGCCCCAAACCAGGGACAGGTGAACCAGTTTTAAG

TTTGCACTACAGCACAGAAGGAACAACTACAAGCACAATAAAACTGAACT

TTACAGATGAATGGAGCAGTATAGCATCAAGTTCTAGAGGAATTGGGAGC

CATTGCAAATCTGAGGGTCAGGAGGAATCTTTCGTCCCACAGAGCTCAGT

GCAACCACCAGAAGGAGACAGTGAAACAAAAGCTCCTGAAGAATCATCAG

AGGATGTGACAAAATATCAGGAAGGAGTATCTGCAGAAAACCCAGTTGAG

AACCATATCAATATAACACAATCAGATAAGTTCACAGCCAAGCCATTGGA

TTCCAACTCAGGAGAAAGAAATGACCTCAATCTTGATCGCTCTTGTGGGG

TTCCAGAAGAATCTGCTTCATCTGAAAAAGCCAAGGAACCAGAAACTTCA

GATCAGACTAGCACTGAGAGTGCTACCAATGAAAATAACACCAATCCTGA

GCCTCAGTTCCAAACAGAAGCCACTGGGCCTTCAGCTCATGAAGAAACAT

CCACCAGGGACTCTGCTCTTCAGGACACAGATGACAGTGATGATGACCCA

GTCCTGATCCCAGGTGCAAGGTATCGAGCAGGACCTGGTGATAGACGCTC

TGCTGTTGCCCGTATTCAGGAGTTCTTCAGACGGAGAAAAGAAAGGAAAG

AAATGGAAGAATTGGATACTTTGAACATTAGAAGGCCGCTAGTAAAAATG

GTTTATAAAGGCCATCGCAACTCCAGGACAATGATAAAAGAAGCCAATTT

CTGGGGTGCTAACTTTGTAATGAGTGGTTCTGACTGTGGCCACATTTTCA

TCTGGGATCGGCACACTGCTGAGCATTTGATGCTTCTGGAAGCTGATAAT

CATGTGGTAAACTGCCTGCAGCCACATCCGTTTGACCCAATTTTAGCCTC

ATCTGGCATAGATTATGACATAAAGATCTGGTCACCATTAGAAGAGTCAA

GGATTTTTAACCGAAAACTTGCTGATGAAGTTATAACTCGAAACGAACTC

ATGCTGGAAGAAACTAGAAACACCATTACAGTTCCAGCCTCTTTCATGTT

GAGGATGTTGGCTTCACTTAATCATATCCGAGCTGACCGGTTGGAGGGTG

ACAGATCAGAAGGCTCTGGTCAAGAGAATGAAAATGAGGATGAGGAA<u>TAA</u>

TAAACTCTTTTTGGCAAGCACTTAAATGTTCTGAAATTTGTATAAGACAT

TTATTATATTTTTTTCTTTACAGAGCTTTAGTGCAATTTTAAGGTTATGG

-continued

```
TTTTTGGAGTTTTTCCCTTTTTTTGGGATAACCTAACATTGGTTTGGAAT

GATTGTGTGCATGAATTTGGGAGATTGTATAAAACAAAACTAGCAGAATG

TTTTTAAAACTTTTTGCCGTGTATGAGGAGTGCTAGAAAATGCAAAGTGC

AATATTTTCCCTAACCTTCAAATGTGGGAGCTTGGATCAATGTTGAAGAA

TAATTTTCATCATAGTGAAAATGTTGGTTCAAATAAATTTCTACACTTGC
```

-continued

```
CATTTGCATGTTTGTTGCTTTCTAATTAAGAAACTGGTTGTTTTAAAAAA

AAAAAAAAGGAATTC
```

The nucleotide sequence encoding the human ARCAP protein (i.e., from the ATG start codon to the codon immediately before the stop codon in SEQ ID NO:3) is designated SEQ ID NO:1. The ARCAP amino acid sequence encoded by the above cDNA is shown below.

```
                                                     (SEQ ID NO:2)
Met ser arg gly gly ser tyr pro his leu leu trp asp val arg lys arg ser leu gly leu glu asp pro ser arg leu arg ser arg tyr leu gly arg arg glu phe ile gln arg leu lys leu glu ala thr leu asn val his asp gly cys val asn thr ile cys trp asn asp thr gly glu tyr ile leu ser gly ser asp asp thr lys leu val ile ser asn pro tyr ser arg lys val leu thr thr ile arg ser gly his arg ala asn ile phe ser ala lys phe leu pro cys thr asn asp lys gln ile val ser cys ser gly asp gly val ile phe tyr thr asn val glu gln asp ala glu thr asn arg gln cys gln phe thr cys his tyr gly thr thr tyr glu ile met thr val pro asn asp pro tyr thr phe leu ser cys gly glu asp gly thr val arg trp phe asp thr arg ile lys thr ser cys thr lys glu asp cys lys asp asp ile leu ile asn cys arg arg ala ala thr ser val ala ile cys pro pro ile pro tyr tyr leu ala val gly cys ser asp ser ser val arg ile tyr asp arg arg met leu gly thr arg ala thr gly asn tyr ala gly arg gly thr thr gly met val ala arg phe ile pro ser his leu asn asn lys ser cys arg val thr ser leu cys tyr ser glu asp gly gln glu ile leu val ser tyr ser ser asp tyr ile tyr leu phe asp pro lys asp asp thr ala arg glu leu lys thr pro ser ala glu glu arg arg glu glu leu arg gln pro pro val lys arg leu arg leu arg gly asp trp ser asp thr gly pro arg ala arg pro glu ser glu arg glu arg asp gly glu gln ser pro asn val ser leu met gln arg met ser asp met leu ser arg trp phe glu glu ala ser glu val ala gln ser asn arg gly arg gly arg ser arg pro arg gly gly thr ser gln ser asp ile ser thr leu pro thr val pro ser ser pro asp leu glu val ser glu thr ala met glu val asp thr pro ala glu gln phe leu gln pro ser thr ser ser thr met ser ala gln ala his ser thr ser ser pro thr glu ser pro his ser thr pro leu leu ser ser pro asp ser glu gln arg gln ser val glu ala ser gly his his thr his his gln ser asp asn asn glu lys leu ser pro lys pro gly thr gly glu pro val leu ser leu his tyr ser thr glu gly thr thr thr ser thr ile lys leu asn phe thr asp glu trp ser ser ile ala ser ser ser arg gly ile gly ser his cys lys ser glu gly gln glu glu ser phe val pro gln ser ser val gln pro pro glu gly asp ser glu thr lys ala pro glu glu ser ser glu asp val thr lys tyr gln glu gly val ser ala glu asn
```

-continued

```
pro val glu asn his ile asn ile thr gln ser asp lys phe thr ala lys pro leu asp ser asn ser gly glu arg asn asp leu asn leu asp arg ser cys gly val pro glu glu ser ala ser ser glu lys ala lys glu pro glu thr ser asp gln thr ser thr glu ser ala thr asn glu asn asn thr asn pro glu pro gln phe gln thr glu ala thr gly pro ser ala his glu glu thr ser thr arg asp ser ala leu gln asp thr asp asp ser asp asp asp pro val leu ile pro gly ala arg tyr arg ala gly pro gly asp arg arg ser ala val ala arg ile gln glu phe phe arg arg arg lys glu arg lys glu met glu glu leu asp thr leu asn ile arg arg pro leu val lys met val tyr lys gly his arg asn ser arg thr met ile lys glu ala asn phe trp gly ala asn phe val met ser gly ser asp cys gly his ile phe ile trp asp arg his thr ala glu his leu met leu leu glu ala asp asn his val val asn cys leu gln pro his pro phe asp pro ile leu ala ser ser gly ile asp tyr asp ile lys ile trp ser pro leu glu glu ser arg ile phe asn arg lys leu ala asp glu val ile thr arg asn glu leu met leu glu glu thr arg asn thr ile thr val pro ala ser phe met leu arg met leu ala ser leu asn his ile arg ala asp arg leu glu gly asp arg ser glu gly ser gly gln glu asn glu asn glu asp glu glu
```

Accordingly, the invention features a substantially pure polypeptide or protein including an amino acid sequence at least 70% (e.g., at least 75, 80, 85, 90, 95, 98, or 100%) identical to SEQ ID NO:2. If the polypeptide includes a sequence that is 100% identical to SEQ ID NO:2, the polypeptide can contain up to 30 conservative amino acid substitutions. The invention also includes a substantially pure polypeptide encoded by a nucleic acid that hybridizes under stringent conditions to a probe the sequence of which consists of SEQ ID NO:1. The polypeptide binds to an androgen receptor and increases the ability of the androgen receptor to transactivate an androgen-responsive gene, as shown in the Example below.

The invention further features an isolated nucleic acid encoding a polypeptide of the invention, a vector including a nucleic acid of the invention, and a cultured host cell containing a nucleic acid of the invention. An example of a nucleic acid within the invention includes an isolated nucleic acid having a strand that hybridizes under stringent conditions to a single stranded probe, the sequence of which consists of SEQ ID NO: 1 or the complement of SEQ ID NO:1. Such a nucleic acid can be at least 15 (e.g., at least 30, 50, 100, 200, 500, or 1000) nucleotides in length.

In addition, the invention features a method of producing a polypeptide by culturing a cultured host cell of the invention in a culture, expressing the polypeptide in the cultured host cell, and isolating the polypeptide from the culture.

The invention also features a method of screening for a compound that decreases androgen receptor-mediated transactivation by contacting a polypeptide of the invention with a protein complex including an androgen receptor, in the presence of a candidate compound; measuring the extent of binding between the polypeptide and the protein complex; and determining whether the extent of binding is less than the extent of binding between the polypeptide and the protein complex in the absence of the candidate compound. An extent of binding in the presence of the compound less than the extent of binding in the absence of the compound indicates that the candidate compound decreases androgen receptor-mediated transactivation.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

A "conservative amino acid substitution" is one in which an amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

By hybridization under "stringent conditions" is meant hybridization at 65° C., 0.5×SSC, followed by washing at 45° C., 0.1×SSC.

The "percent identity" of two amino acid sequences or of two nucleic acids is determined using the algorithm of Karlin and Altschul (Proc. Natl. Acad. Sci. USA 87:2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12. BLAST protein searches are performed with the XBLAST program, score=50, wordlength=3. Where gaps exist between two sequences, Gapped BLAST is utilized as described in Altschul et al. (Nucleic Acids Res. 25:3389–3402, 1997). When utilizing BLAST and Gapped BLAST programs, the default parameters of the respective programs (e.g., XBLAST and NBLAST) are used. See http://www.ncbi.nlm.nih.gov.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones, e.g., as these occur in a DNA library such as a cDNA or genomic DNA library.

The polypeptides of the invention can be used to generate antibodies (either monoclonal or polyclonal) that specifically bind to ARCAP protein. These antibodies in turn are useful for detecting the presence and distribution of ARCAP in tissues and in cellular compartments. For example, such antibodies can be used to diagnose cancerous liver tissue by determining whether ARCAP protein is expressed or overexpressed in the tissue. Similarly, the nucleic acids of the invention can be used to diagnose liver cancer by determining whether ARCAP mRNA is being expressed or overexpressed in a tissue or cell. The nucleic acids can be used as primers in PCR-based detection methods, or as labeled probes in nucleic acid blots (e.g., Northern blots).

Other features or advantages of the present invention will be apparent from the following detailed description, and also from the claims.

DETAILED DESCRIPTION

The invention relates to new ARCAP proteins and nucleic acids encoding them that are overexpressed in hepatocellular carcinoma cells relative to normal liver cells. In addition to differential expression, ARCAP was found to bind to and augment the transactivation activity of an androgen receptor. These observations and others described below suggest that ARCAP activates, via an androgen receptor complex, mitogenic genes that are androgen-responsive (i.e., genes whose promoters contain androgen responsive elements), that overexpression of ARCAP leads to cancer by facilitating androgen receptor-mediated transactivation of androgen-responsive mitogenic genes, and that inhibition of ARCAP expression or activity would reduce expression of these androgen-responsive mitogenic genes and revert cancer cells to a more normal phenotype. Consequently, ARCAP is a new cancer drug target.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express an ARCAP protein (e.g., via a recombinant expression vector in a host cell in gene therapy applications), to detect an ARCAP mRNA (e.g., in a biological sample) or a genetic alteration in an ARCAP gene, and to modulate ARCAP activity. The ARCAP proteins can be used to treat disorders characterized by insufficient or excessive production of an ARCAP substrate or production of ARCAP inhibitors. In addition, the ARCAP proteins can be used to screen for naturally occurring ARCAP substrates, to screen for drugs or compounds which modulate ARCAP activity, as well as to treat disorders characterized by insufficient or excessive production of ARCAP protein or production of ARCAP protein forms that have decreased, aberrant, or unwanted activity compared to ARCAP wild type protein (e.g., in liver cancer). Moreover, the anti-ARCAP antibodies of the invention can be used to detect and isolate ARCAP proteins, regulate the bioavailability of ARCAP proteins, and modulate ARCAP activity.

A method of evaluating a compound for the ability to interact with, e.g., bind, a subject ARCAP polypeptide is provided. The method includes: contacting the compound with the subject ARCAP polypeptide; and evaluating ability of the compound to interact with, e.g., to bind or form a complex with, the subject ARCAP polypeptide. This method can be performed in vitro, e.g., in a cell free system, or in vivo, e.g., in a two-hybrid interaction trap assay. This method can be used to identify naturally occurring molecules that interact with subject ARCAP polypeptide. It can also be used to find natural or synthetic inhibitors of a subject ARCAP polypeptide.

Screening Assays

The invention provides methods (also referred to herein as "screening assays") for identifying modulators, i.e., candidate or test compounds or agents (e.g., proteins, peptides, peptidomimetics, peptoids, small molecules, or other drugs) which bind to ARCAP proteins, have a stimulatory or inhibitory effect on, for example, ARCAP expression or ARCAP activity, or have a stimulatory or inhibitory effect on, for example, the expression or activity of an ARCAP substrate. Compounds thus identified can be used to modulate the activity of target gene products (e.g., ARCAP genes) in a therapeutic protocol, to elaborate the biological function of the target gene product, or to identify compounds that disrupt normal target gene interactions.

In one embodiment, the invention provides assays for screening candidate or test compounds which are substrates of an ARCAP protein or polypeptide or a biologically active portion thereof. In another embodiment, the invention provides assays for screening candidate or test compounds which bind to or modulate the activity of an ARCAP protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which is resistant to enzymatic degradation but which nevertheless remains bioactive; see, e.g., Zuckermann, R. N. et al. (1994) *J. Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer, or small molecule libraries of compounds (Lam, K. S. (1997) *Anticancer Drug Des.* 12:145).

Examples of methods for the synthesis of molecular libraries can be found in the art, for example in DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), on beads (Lam (1991) *Nature* 354:82–84), chips (Fodor (1993) *Nature* 364:555–556), bacteria (Ladner, U.S. Pat. No. 5,223,409), spores (Ladner U.S. Pat. No. '409), plasmids (Cull et al. (1992) *Proc Natl Acad Sci USA* 89:1865–1869), or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; Ladner supra.).

In one embodiment, an assay is a cell-based assay in which a cell which expresses an ARCAP protein or biologically active portion thereof is contacted with a test compound, and the ability of the test compound to modulate ARCAP activity is determined. Determining the ability of the test compound to modulate ARCAP activity can be accomplished by monitoring, for example, cell cycle-regulated cellular localization. The cell, for example, can be of mammalian origin, e.g., human.

The ability of the test compound to modulate ARCAP binding to a compound, e.g., an androgen receptor complex, or to bind to ARCAP can also be evaluated. This can be accomplished, for example, by coupling the compound, e.g., the substrate, with a radioisotope or enzymatic label such that binding of the compound, e.g., the substrate, to ARCAP can be determined by detecting the labeled compound, e.g., substrate, in a complex. Alternatively, ARCAP could be coupled with a radioisotope or enzymatic label to monitor the ability of a test compound to modulate ARCAP binding to an ARCAP substrate in a complex. For example, compounds (e.g., ARCAP substrates) can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., an ARCAP substrate) to interact with ARCAP with or without the labeling of any of the interactants can be evaluated. For example, a microphysiometer can be used to detect the interaction of a compound with ARCAP without the labeling of either the compound or the ARCAP. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and ARCAP.

In yet another embodiment, a cell-free assay is provided in which an ARCAP protein or biologically active portion thereof is contacted with a test compound and the ability of the test compound to bind to the ARCAP protein or biologically active portion thereof is evaluated. Preferred biologically active portions of the ARCAP proteins to be used in assays of the present invention include fragments which participate in interactions with non-ARCAP molecules, e.g., fragments with high surface probability scores.

Soluble and/or membrane-bound forms of isolated proteins (e.g., ARCAP proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl-N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor.' Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the ARCAP protein to bind to a target molecule can be accomplished using real-time Biomolecular Interaction Analysis (BIA) (see, e.g., Sjolander, S. and Urbaniczky, C. (1991) *Anal. Chem.* 63:2338–2345 and Szabo et al. (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either ARCAP, an anti-ARCAP antibody or its target molecule to facilitate separation of complexed from uncomplexed forms of one or both of the proteins, as well as to accommodate automation of the assay. Binding of a test compound to an ARCAP protein, or interaction of an ARCAP protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/ARCAP fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or ARCAP protein, and the mixture incubated under conditions conducive to complex formation (e.g., at physiological conditions for salt and pH). Following incubation, the beads or microtiter plate wells are washed to remove any unbound components, the matrix immobilized in the case of beads. Complexes are determined either directly or indirectly, for example, as described above. Alternatively, the complexes can be dissociated from the matrix, and the level of ARCAP binding or activity determined using standard techniques.

Other techniques for immobilizing either an ARCAP protein or a target molecule on matrices include using conjugation of biotin and streptavidin. Biotinylated ARCAP protein or target molecules can be prepared from biotin-NHS(N-hydroxy-succinimide) using techniques known in the art (e.g., biotinylation kit, Pierce Chemicals, Rockford, IL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with ARCAP protein or target molecules but which do not interfere with binding of the ARCAP protein to its target molecule. Such antibodies can be derivatized to the wells of the plate, and unbound target or ARCAP protein trapped in the wells by antibody conjugation. Methods for detecting such complexes, in addition to those described above for the GST-immobilized complexes, include immunodetection of complexes using antibodies reactive with the ARCAP protein or target molecule, as well as enzyme-linked assays which rely on detecting an enzymatic activity associated with the ARCAP protein or target molecule.

Alternatively, cell free assays can be conducted in a liquid phase. In such an assay, the reaction products are separated from unreacted components by any of a number of standard techniques including but not limited to differential centrifugation (see, for example, Rivas, G., and Minton, A. P., (1993) *Trends Biochem Sci* 18:284–7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11:141–8; Hage, D. S., and Tweed, S. A. (1997) *J Chromatogr B Biomed Sci Appl.* 699:499–525). Further, fluorescence energy transfer may also be conveniently utilized, as described herein, to detect binding without further purification of the complex from solution.

In a preferred embodiment, the assay includes contacting the ARCAP protein or biologically active portion thereof with a known compound (e.g., an androgen receptor) which binds ARCAP to form an assay mixture, contacting the assay mixture with a test compound, and determining the ability of the test compound to interact with an ARCAP protein, where determining the ability of the test compound to interact with an ARCAP protein includes determining the ability of the test compound to preferentially bind to ARCAP or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the ARCAP genes herein identified. In an alternative embodiment, the invention provides methods for determining the ability of the test compound to modulate the activity of an ARCAP protein through modulation of the activity of a downstream effector of an ARCAP target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form a complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases where it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner is anchored onto a solid surface (e.g., a microtiter plate), while the non-anchored species is labeled either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface, e.g., using a labeled antibody specific for the initially non-immobilized species. The antibody, in turn, can be directly labeled or indirectly labeled with, e.g., a labeled anti-Ig antibody. Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected, e.g., using an immobilized antibody specific for one of the binding components to anchor any complexes formed in solution and a labeled antibody specific for the other partner to detect anchored complexes. Again, depending upon the order of addition of reactants to the liquid phase, test compounds that inhibit complex formation or that disrupt preformed complexes can be identified.

In an alternate embodiment, a homogeneous assay can be used. For example, a preformed complex of the target gene product and the interactive cellular or extracellular binding partner product is prepared so that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the ARCAP proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268: 12046–12054; Bartel et al. (1993) *Biotechniques* 14:920–924; Iwabuchi et al. (1993) *Oncogene* 8:1693–1696; and Brent WO94/10300) to identify other proteins, which bind to or interact with ARCAP ("ARCAP-binding proteins" or "ARCAP-bp") and are involved in ARCAP activity. Such ARCAP-bps can be activators or inhibitors of signals by the ARCAP proteins or ARCAP targets as, for example, downstream elements of an ARCAP-mediated signaling pathway.

The two-hybrid system is based on the modular nature of most transcription factors, which consist of separable DNA-binding and activation domains. Briefly, the assay utilizes two different DNA constructs. In one construct, the gene that codes for an ARCAP protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively, the ARCAP protein can be fused to the activator domain.) If the "bait" and the "prey" proteins are able to interact, in vivo, forming an ARCAP-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein that interacts with the ARCAP protein.

In another embodiment, modulators of ARCAP expression are identified. For example, a cell or cell free mixture is contacted with a candidate compound and the expression of ARCAP mRNA or protein evaluated relative to the level of expression of ARCAP mRNA or protein in the absence of the candidate compound. When expression of ARCAP mRNA or protein is greater in the presence of the candidate compound than in its absence, the candidate compound is identified as a stimulator of ARCAP mRNA or protein expression. Alternatively, when expression of ARCAP mRNA or protein is less (statistically significantly less) in the presence of the candidate compound than in its absence, the candidate compound is identified as an inhibitor of ARCAP mRNA or protein expression. The level of ARCAP mRNA or protein expression can be determined by methods described herein for detecting ARCAP mRNA or protein.

In another aspect, the invention pertains to a combination of two or more of the assays described herein. For example, a modulating agent can be identified using a cell-based or a cell free assay, and the ability of the agent to modulate the activity of an ARCAP protein can be confirmed in vivo, e.g., in an animal such as an animal model for hepatocellular carcinoma.

This invention further pertains to novel agents identified by the above-described screening assays. Accordingly, it is within the scope of this invention to further use an agent identified as described herein (e.g., an ARCAP modulating agent, an antisense ARCAP nucleic acid molecule, an ARCAP-specific antibody, or an ARCAP-binding partner) in an appropriate animal model to determine the efficacy, toxicity, side effects, or mechanism of action, of treatment with such an agent. Furthermore, novel agents identified by the above-described screening assays can be used for treating cancers, e.g., liver cancer.

Use of ARCAP Molecules as Surrogate Markers

The ARCAP molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the ARCAP molecules of the invention may be detected, and may be correlated with one or more biological states in vivo. For example, the ARCAP molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a liver tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include those described in Koomen et al. (2000) *J. Mass. Spectrom.* 35: 258–264; and James (1994) *AIDS Treatment News Archive* 209.

The ARCAP molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., an ARCAP marker) transcription or expression, the amplified marker may be in a quantity which is more readily detectable than the drug itself. Also, the marker may be more easily detected due to the nature of the marker itself; for example, using the methods described herein, anti-ARCAP antibodies may be employed in an immune-based detection system for an ARCAP protein marker, or ARCAP-specific radiolabeled probes may be used to detect an ARCAP mRNA marker. Furthermore, the use of a pharmacodynamic marker may offer mechanism-based prediction of risk due to drug treatment beyond the range of possible direct observations. Examples of the use of pharmacodynamic markers in the art are described in Matsuda et al. U.S. Pat. No. 6,033,862; Hattis et al. (1991) Env. Health Perspect. 90: 229–238; Schentag (1999) *Am. J. Health-Syst. Pharm.* 56 Suppl. 3: S21–S24; and Nicolau (1999) *Am, J. Health-Syst. Pharm.* 56 Suppl. 3: S16–S20.

The ARCAP molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., ARCAP protein or RNA) for specific tumor markers in a subject, a drug or course of treatment may be selected which is optimized for the treatment of the specific tumor likely to be present in the subject. Similarly, the presence or absence of a specific sequence mutation in ARCAP DNA may correlate with ARCAP drug response. The use of pharmacogenomic markers therefore permits the application of the most appropriate treatment for each subject without having to administer the therapy.

Pharmacogenomics

The ARCAP molecules of the present invention, as well as agents, or modulators which have a stimulatory or inhibitory effect on ARCAP activity (e.g., ARCAP gene expression) as identified by a screening assay described herein can be administered to individuals to treat (prophylactically or therapeutically) ARCAP associated disorders (e.g., liver cancer) associated with aberrant or unwanted ARCAP activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer an ARCAP molecule or ARCAP modulator as well as tailoring the dosage and/or therapeutic regimen of treatment with an ARCAP molecule or ARCAP modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23:983–985 and Linder, M. W. et al. (1997) Clin. Chem. 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association," relies primarily on a high-resolution map of the human genome consisting of already known gene-related markers (e.g., a "bi-allelic" gene marker map which consists of 60,000–100,000 polymorphic or variable sites on the human genome, each of which has two variants). Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., an ARCAP protein of the present invention), all common variants of that gene can be fairly easily identified in the population, and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., an ARCAP molecule or ARCAP modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with an ARCAP molecule or ARCAP modulator, such as a modulator identified by one of the exemplary screening assays described herein.

The present invention further provides methods for identifying new agents, or combinations, that are based on identifying agents that modulate the activity of one or more of the gene products encoded by one or more of the ARCAP genes of the present invention, where these products may be associated with resistance of the cells to a therapeutic agent. Specifically, the activity of the proteins encoded by the ARCAP genes of the present invention can be used as a basis for identifying agents for overcoming agent resistance. By blocking the activity of one or more of the resistance proteins, target cells, e.g., human cells, will become sensitive to treatment with an agent that the unmodified target cells were resistant to.

Monitoring the influence of agents (e.g., drugs) on the expression or activity of an ARCAP protein can be applied in clinical trials. For example, the effectiveness of an agent determined by a screening assay as described herein to increase ARCAP gene expression, protein levels, an ARCAP activity can be monitored in clinical trials of subjects exhibiting decreased ARCAP gene expression, protein levels, or ARCAP activity. Alternatively, the effectiveness of an agent determined by a screening assay to decrease ARCAP gene expression, protein levels, or an ARCAP activity can be monitored in clinical trials of subjects exhibiting increased ARCAP gene expression, protein levels, or ARCAP activity. In such clinical trials, the expression or activity of an ARCAP gene, and preferably other genes that have been implicated in, for example, an ARCAP-associated disorder can be used as a "read out" or marker of the phenotype of a particular cell.

Without further elaboration, it is believed that one skilled in the art can, based on the above disclosure and the example below, utilize the present invention to its fullest extent. The following examples are to be construed as merely illustrative of how one skilled in the art can isolate and use the polypeptides and nucleic acids of the invention, and are not limitative of the remainder of the disclosure in any way. Any publications cited in this disclosure are hereby incorporated by reference.

EXAMPLE

Materials and Methods

Patient samples. Hepatocellular carcinoma patients from the Department of Surgery, Veterans General Hospital, Taipei, Taiwan, were recruited into this study. Diagnosis of hepatoma was made by sonography, angiography, computer tomography, and/or magnetic resonance imaging. Clinical information for each patient was recorded, including the patients' age, sex, serum alpha-fetoprotein level, liver function, tumor size, tumor location, pathological staging, disease-free interval, time of recurrence, and location of tumor recurrence. Informed consent was obtained from each patient. For each liver cancer patient, tissue was harvested from the tumor, as well as from the normal liver tissue that was adjacent to the tumor.

RNA extraction and reverse transcription for complement DNA. Tissue specimens were frozen immediately after surgical resection and stored at −80° C. RNA was extracted using acid guanidinium thiocyanate and phenol/chloroform extraction as described in Chomczynski et al. (1987) Anal. Biochem. 162:156–159. Approximately 0.5 g of frozen tissue was homogenized with 4 ml RNAzol B (Biotecx Laboratories, Houston, Tex.) using a polytron. DNA was sheared using a Douncer with a type-B pestle. After adding 0.4 ml of chloroform, vigorous vortexing, and standing on ice for 5 minutes, the mixture was separated by centrifugation at 12,000 g at 4° C. for 15 minutes. The upper aqueous phase containing total RNA was precipitated with an equal volume of isopropanol.

Complement DNA was synthesized from the 1 µg of total RNA. Reverse transcription was performed in a volume of 30 µl, containing RNA and 1× first strand buffer (10 mM DTT, 500 µM dNTPs, 50 ng/ml oligo-dT, and 100 units MMLV reverse transcriptase) at 37° C. for 1 hour (Life Technologies). The samples were then denatured at 95° C. for 5 minutes.

PCR amplification. cDNA (1 µl) was PCR amplified in a volume of 25 µl containing 0.8 µM of primers, 50 µM of each dNTP (Takara), 1×PCR buffer, and 1.25 units Taq Polymerase (Pharmacia). As a control for cDNA quality, a test PCR reaction was carried out using the human transferrin gene primers Tref8 (GGAACATTTTGGCAAA-GACA [SEQ ID NO:4]; derived from nucleotides 971–990 of the transferring cDNA sequence) and Tref9 (ATTCAT-GATCTT(C/T)GCGATGC [SEQ ID NO:5]; derived from nucleotides 1307–1288 of the transferrin cDNA sequence). These primer sequences were chosen form the eighth and ninth exons of the human transferrin gene, respectively. PCR was performed using an initial denaturation at 94° C. for 10 minutes; followed by 30 cycles of 94° C. for 1 minutes, 55° C. for 1 minute, and 72° C. for 1 minute; then a final extension at 72° C. for 10 minutes. A successful PCR yielded a 336 bp product, indicating that the cDNA template is at least 1.4 kb from the poly(A) end (nt 2362).

The steroid receptor superfamily clones were generated by amino acid-based homology PCR using degenerate primers encoding highly conserved sequence motifs in the zinc finger of DNA binding domain of steroid receptors. The primers encoded the amino acid sequences DYSTGYHY (SEQ ID NO:6), CKXFFKR (SEQ ID NO:7), and CPACR-FXKC (SEQ ID NO:8), all of which are described in Maksymowych et al (1992) *Receptor* 2:225–240. The forward and reverse primer sequences were RCAYTTIIIIAR-ICKRCAIKMNKGRCA (SEQ ID NO:11), and GAYRARKC1WCIGGIWRICAYT (SEQ ID NO:12). PCR was performed under low stringency annealing/extension conditions (42° C./65° C.) for 5 cycles, before amplifying the templates at high-stringency conditions (55° C./72° C.). The PCR products were subcloned into the TA vector (Invitrogen), and the resulting plasmid used to transform DH5α cells. Clones were randomly picked and checked for an insert size of about 170 bp, a length corresponding to a zinc finger. A high frequency of clones contained appropriately sized inserts (85–90%).

DNA Sequence Analysis of novel ARCAP. Positive clones were picked and sequenced using Applied Biosystems model 377 DNA sequencers. The cloned sequences were analyzed using the BLASTN program (Zehetner et al. (1994) *Nature* 367:489–491). Partial cDNA clones bearing sequence similarity to members of the steroid receptor superfamily were selected for further study. Of these clones, one clone named ARCAP, was characterized and fully cloned as described herein.

Isolation of full length clone. To obtain the complete open reading frame of ARCAP, a commercial cDNA library of G2 hepatoma cell line (Clontech) was probed with the ARCAP partial clone. In addition, hepatoma cDNA libraries were constructed from RNA isolated from a hepatoma tumor and normal human liver tissue, both donated by a male patient that died from trauma. Approximately 5 µg of mRNA was used for reverse transcription. The cDNA library was prepared using the lambda ZAP II system (Stratagene). The library was amplified from $1.1\times10^6$ PFU of primary recombinant clones. The average insert size was 1.2 kb. More than 95% of the clones are recombinants.

To isolate novel clones from the liver cDNA libraries, radio-labeled probes were prepared using a PCR reaction supplemented with a $^{32}$P-labeled dCTP. Specifically, a labeling reaction of 100 µl volume contained 1× buffer (1.5 µM $MgCl_2$, 0.5 µl Taq polymerase (25 units/ml), 200 µM each of dGTP, dTTP, and dATP, and 25–50 µM dCTP) and 5 µl of $^{32}$P-α-dCTP. The PCR conditions for producing labeled probes was essentially the same as described above for amplifying steroid receptor clones based on conserved domains.

The cDNA library was screened at a moderate density (16,000 PFU per 150 mm plate). Twenty plates were initially screened. Pre-hybridization was carried out in 5×SSC, 2× Denhardt's, 100 mg/ml single-stranded salmon sperm DNA, and 0.1% SDS at 55° C. Hybridization was performed in the same solution but supplemented with $1\times10^7$ cpm/ml solution of denatured PCR-labeled probes. After incubation at 55° C. for 20 hours, low stringency washing was performed for 60 minutes at room temperature using 2×SSC, 0.1% SDS. The blots were visualized by autoradiography (24 hours exposure) using Kodak X-AR film and one intensifying screen (Lighting Plus).

Cloning by 5'-RACE and 3'-RACE. RACE is a procedure for amplification of a cDNA template between a known internal site and unknown sequences at either 5' or the 3' ends (Fronhman et al., (1988) *Proc. Natl. Acad. Sci. USA* 85:8998–9001). The basic protocol performed in this study was described in the literature accompanying Clontech's RACE kits.

GSP1 (TCTGGTGGTTGCACTGAGCT; SEQ ID NO:13) and GSP2 (ACAATGTCAGCTCAGGCTC; SEQ ID NO:14) primers were designed in-house and based on the sequence of ARCAP. Human hepatoma cell line G2 mRNA was used as template for synthesis of first strand cDNA. This synthesis was performed using primers 3'-CDS (AAG-CAGTGGTAACAACGCAGAGTACT$_{30}$NN; SEQ ID NO:15) for 3' RACE or Smart-oligo ($T_{25}$NN; SEQ ID NO:16) plus 5'-CDS (AAGCAGTGGTAACAACGCAGAG TACGCGGG; SEQ ID NO:17) for 5' RACE.

After synthesis of first strand cDNA, 5' RACE was performed by PCR using Smart and GSP1 primers. For 3' RACE, PCR was performed using GSP2 and 3'CDS primers. Each fragment after PCR were cloning into pGEM-easy vector (Promega). After screening, the correct clones were picked, and plasmid DNAs were purified. The full length ARCAP cDNA sequence was thus obtained.

Production of ARCAP antibody. The ARCAP clone was digested with EcoR1 and inserted into pGEX2T to produce a ARCAP-GST expression plasmid (Pharmacia). This plasmid was used to transform BL21 bacteria, which were then induced using IPTG to express the fusion protein. The fusion protein was purified from bacterial lysate using Glutathione Sepharose 4B affinity chromatography. The ARCAP protein was detected by Western blotting using an anti-GST antibody. Twenty micrograms of fusion protein was injected into Balb/c mice to raise ARCAP antiserum.

ARCAP expression analysis. To determine the mRNA expression pattern for ARCAP, RNA samples prepared from tissues and cell lines were analyzed by Northern blot. Twenty micrograms each of total RNA from liver, fetal brain, four cell lines derived from liver (HepG2, Hep3B, VGH/22T, VGH/59T), blood cell lines (K562, U932, Ramos, Jurkat), and HeLa cells were separated on a formaldehyde gel and transferred to a filter membrane. Filter hybridization was carried out with the labeled probes at 42° C. in 5×SSC, 5× Denhardt's, 5 mg/ml denatured salmon sperm DNA, 50% formamide, and 0.1% SDS. Washing was first performed at room temperature in 2×SSC/0.1% SDS for 30 minutes, followed by washing at 42° C. in 2×SSC/0.1% SDS for 30 minutes, and then a final washing at 55° C. in 0.2×SSC/0.1% SDS for 30 minutes. Autoradiography film was exposed using one intensifying screen for 72 hours.

For in situ hybridization, liver cancer tissue sections were obtained from the patient samples described above. A riboprobe of ARCAP was prepared using the partial ARCAP clone and a biotin labeling kit (NEN). Hybridization and washes were carried out according to established protocols. For ARCAP protein expression, an antibody was raised using a GST-ARCAP fusion expression vector as described herein. This antibody was then used to identify the presence of ARCAP protein in the various tissue sections.

ARCAP *transactivation of androgen-responsive genes*. COS-1 cells were cultured for at least 48 hours before transfection in Dulbecco's modified Eagle's medium (Life Technologies, Inc.) supplemented with 10% fetal calf serum that had been stripped of steroids by treatment with dextran-coated charcoal. Cells were grown to 60–80% confluence, washed, removed, and seeded at a density of $5\times10^4$ cells/well in fresh medium in 35 mm wells (Corning) of a microtitre tissue culture plate. After 20 hours, cells were washed once with serum-free medium and transfected using Fugene 6 (Roche) according to the manufacturer's directions. Ten hours thereafter, cells were washed twice with the appropriate medium and incubated in 2 ml of medium containing steroid or vehicle. After 48 hours, cells were recovered and assayed for luciferase activity according to the manufacturer's instructions (Promega).

Luciferase activity was corrected for the corresponding β-galactosidase activity to give relative activity. β-Galactosidase assays were performed in a 96-well plate (Corning) as follows: 10 μl of sample extract were incubated with 80 μl of buffer Z and 10 μl of o-nitrophenyl-β-D-galactopyranoside (4 mg/ml) at 30° C. for 2 hours. The reaction was terminated by the addition of 50 μl of 1 M $Na_2CO_3$. $A_{420}$ values were obtained using a MR5000 plate reader (Dynatech), and activity was calculated as described herein. Transfections were performed in triplicate and repeated at least three times.

Hepatoma A2 cells were subcultured in DMEM medium (Life Technologies, Inc.) supplemented with 10% fetal calf serum. Cells were seeded at $1\times10^5$ cells/well in 35 mm wells at least 24 hours before transfection. For studies examining the interaction between AR and ARCAP-1, cells were cultured in DMEM supplemented with 10% dextran-coated charcoal-fetal calf serum. Cells were transfected using Fugene 6 for a period of 8 hours, washed, and cultured in medium containing vehicle or steroid. Cells were harvested at 48 hours after transfection and analyzed as described above.

A 450 base fragment containing an androgen-responsive element (TGGGTACATTTTGTTC; SEQ ID NO:9) from a portion of the human alpha-fetoprotein promoter 4385 bp from the ATG start coding site (Genbank ID: G178242) was found to have transactivation response ability when cloned into a heterologous gene. This fragment was amplified by PCR from human genomic DNA (Clontech). A element androgen responsive element containing the sequence TGGGTA<u>GG</u>TTTTGCTC (SEQ ID NO:10) was made by site direct mutagenesis. The mutated nucleotides are indicated by underlining. This product was cloned into the pGEM-easy vector (Promega), and the sequence of the element was confirmed by sequencing. The inserted DNA were subcloned into the appropriate sites in the luciferase reporter plasmid pGL3basic (Promega).

AR and ARCAP were fused in frame to the amino terminus of enhanced GFP (EGFP) in the vector pEGFP—N1 (Clontech) using an EcoRI site. This plasmid was used to transform into *E. coli* (DH5). Positive clones were identified using mini-plasmid preparation and restriction enzyme analysis. Selected constructs were confirmed by sequencing. COS7 and A2 cells were cultured in DMEM supplemented with 10% fetal calf serum, penicillin/streptomycin (100 μg/ml), and L-glutamine (2 mM). Subconfluent monolayers ($10^6$ cells in 100 mm dishes) were transfected with 10 μg of AR and ARCAP cDNA by calcium phosphate. Thirty hours later, fresh media were replaced with medium supplemented with DHT (10 nM). The cells were observed using a fluorescence microscope (Nikon).

Immunoprecipitations. Expression plasmids encoding androgen receptor, ARA70, and ARCAP-HA or ARCAP-Xpress epitope fusion protein were produced in pCDNA III (Invitrogen) using EcoRI. After transfection into COS7 cells, protein was labeled using the in vitro-coupled transcription and translation kit, T7-TNT (Promega), for incorporating $^{35}S$-methione. At 48 hours post-transfection, the cultures were supplemented to 10 nM DHT. Cells were lysed, and the lysate was incubated with 1 ml of immunoprecipitation buffer (50 mM Tris, pH 7.5, 150 mM NaCl, 0.2 mM $Na_3VO_4$, 0.5% Nonidet P-40, 1 mM phenylmethylsulfonyl fluoride, 1 mM dithiothreitol, 25 μg/ml leupeptin, 25 μg/ml aprotinin, and 25 μg/ml pepstatin). The lysate was then mixed and incubated with AR, HA, or Xpress antibody (Invitrogen) on ice for 60 minutes, at which time 10 μl of protein A-sepharose beads (Pharmacia) were added. The immunoprecipitations were incubated for 16 hours at 4° C. with continuous mixing. Immunoprecipitated complexes were collected by centrifugation at 2000 rpm at 4° C. for 10 minutes. The pelleted beads were washed three times and mixed with SDS sample buffer. Samples were resolved on 8% polyacrylamide gels at 200 V for 45 minutes. The gel was fixed for 30 minutes in 10% propanol and 10% acetic acid, soaked in Amplify (Amersham Pharmacia Biotech) for 30 minutes, dried under vacuum, and exposed to X-ray film for 4 to 24 hours at 70° C.

Yeast two hybrid analysis. For independent cloning of ARCAP, androgen receptor was used as a bait to screen the matchmaker yeast two hybrid library (Clontech). Briefly, the full length insert of androgen receptor sequence was cloned into pS2-1 (Clontech), and the resulting construct used to screen a yeast-two hybrid testis library constructed in pACT2 (Clontech), using the yeast host Y187, according to the manufacturer's protocols. Two hundred thousand transformed cells were plated onto media lacking tryptophan, leucine, and adenine, but supplement with 1 μM dihydrotestosterone (DHT). Adenine-positive, LacZ-positive, histidine-positive colonies were isolated, and plasmid DNA obtained therefrom. The plasmids were transformed into *E. coli*.

pACT2 plasmids containing cDNA were identified by colony PCR using primers specific for the LEU2 gene present in pACT2. Specificity of interaction for with the human androgen receptor (hAR) was determined by examining the liquid LacZ activity of cDNA clones in the presence of the GAL4 DBD:hAR fusion protein versus the activity observed in the presence of the GAL4 DBD alone.

After sequencing and examination of the GenBank database, it was determined that one interacting clone was encoded by ARCAP.

The yeast two-hybrid system was also actively used to confirm the interaction of ARCAP with hAR. pAS2-con-structs were co-transformed with pACT2-ARCAP or pACT2 alone into yeast host Y1187 according to the manufacturer's protocol (Clontech). Trp-positive, Leu-positive colonies were inoculated in triplicate onto selective media and grown at 30° C. overnight in the presence or absence of 1 µM DHT. Samples were diluted to an $A_{600}$ of 0.2 and re-grown to an $A_{600}$ of 0.6–0.8. Samples were divided into three aliquots of 1 ml each. Cells were recovered by centrifugation at 14,000 rpm for 5 minutes, washed once with buffer Z (0.1 M sodium phosphate, pH 7.0, 10 mM KCl, and 10 mM $MgSO_4$), and resuspended in 800 µl of buffer Z containing 21 µl of 2-mercaptoethanol. Then 10 µl of 0.1% SDS were added, followed by the addition of 50 µl of chloroform. Samples were vortexed for 1 minute and incubated at 30° C., and then 200 µl of o-nitrophenyl-β-D-galactopyranoside (4 mg/ml in buffer Z) were added. Reactions were timed and terminated upon observing an obvious yellow color or after 1 hour by the addition of 500 µl of 1 M $Na_2CO_3$. $A_{420}$ of the samples was determined, and activity was calculated as follows: $(A_{420} \times 1000)/(A_{600} \times time)$. All assays were performed in triplicate and repeated at least three times.

Results

The full length ARCAP cDNA and the protein it encodes is described above.

ARCAP mRNA levels were assessed in normal human tissues and in various cell lines, including hepatoma cell lines, using Northern blotting. ARCAP was detected only in normal human heart and skeletal muscle tissues. High levels of ARCAP expression was detected in hepatoma cells including 3B, 22T, Huh 7, G2, and A2.

Paired liver tumor and normal tissue adjacent to the tumor were isolated from 40 liver cancer patients. Using Northern blotting, it was discovered that ARCAP mRNA was generally highly expressed in the tumor but expressed very little, if at all, in the adjacent normal liver tissue. Using ARCAP-specific antibodies, the presence of ARCAP protein in tumor tissue and the general absence of ARCAP protein in the adjacent normal tissue was confirmed. In situ hybridization of ARCAP mRNA in human hepatoma tissues also indicated that ARCAP mRNA was abundant in tumor cells but rare in normal cells. These data concerning the expression profile of ARCAP mRNA and protein indicated that ARCAP expression is a marker for liver cancer.

To determine cellular localization of ARCAP protein, the ARCAP coding region was fused to GFP in an expression vector, and the vector transfected into human hepatoma A2 cells. The fusion protein was localized in the nucleus, indicating that ARCAP is a nuclear protein.

A yeast two hybrid system was used to determine whether ARCAP binds to androgen receptor. A full length androgen receptor was cloned adjacent to a GAL4 DNA binding domain and used as a bait to screen for His3-positives clones from the human matchmaker liver library (Clontech). The interaction of AR and ARCAP in vivo was confirmed by this study. To further confirm that ARCAP binds to the androgen receptor, ARCAP and the androgen receptor were co-expressed as fusion proteins. Since immunoprecipitation of androgen receptor led to isolation of ARCAP and immunoprecipitation of ARCAP led to isolation of androgen receptor, the physical interaction of ARCAP and androgen receptor was confirmed.

To determine whether the physical association between the androgen receptor and ARCAP protein was biochemically significant, the α-fetoprotein gene promoter was used in a luciferase reporter construct. The α-fetoprotein (AFP) gene is a model system for the studying developmental control of gene expression. AFP is expressed at a high level in fetal liver, but its transcription declines rapidly after birth and is hardly detectable in adult life. However, the AFP gene is often reactivated to a high level when hepatomas or teratomas develop (Shulman et al. (1995) *Proc. Natl. Acad. Sci. USA* 92:8288–8292). An enhancer region in the AFP promoter contains an androgen responsive element (ARE). A control isogenic luciferase reporter containing a mutated ARE was also used in the study to determine whether the ARE was responsible for mediating any biochemical effects.

G2 cells were transfected with the wild type or control reporter and (1) mock DNA, (2) DNA encoding androgen receptor, (3) DNA encoding ARCAP, or (4) DNA encoding androgen receptor and DNA encoding ARCAP. Little change in luciferase activity was observed when the control reporter was used. However, using the wild type reporter, luciferase activity was increased at least 2× (relative to the control reporter) when androgen receptor was expressed. Surprisingly, the simultaneous expression of androgen receptor and ARCAP resulted in about a 3–4 fold increase in luciferase activity, relative to the control reporter containing the mutated ARE. This result indicated that ARCAP augments the transactivation activity of androgen receptor on the AFP promoter.

The above AFP reporter experiments were performed in the presence of testosterone. To confirm that this effect was dependent on formation of the testosterone/androgen receptor complex, the wild type reporter was co-transfected with (1) mock DNA, (2) DNA encoding androgen receptor, (3) DNA encoding ARCAP, or (4) DNA encoding androgen receptor and DNA encoding ARCAP, in the presence or absence of testosterone. The results clearly indicated that the enhanced transactivation activity for androgen receptor due to ARCAP was dependent on testosterone.

OTHER EMBODIMENTS

It is to be understood that while the invention has been described in conjunction with the detailed description thereof, the foregoing description is intended to illustrate and not limit the invention, which is defined by the scope of the appended claims. Other aspects, advantages, and modifications are within the scope of this invention.

What is claimed is:

1. A substantially pure polypeptide comprising the amino acid sequence of SEQ ID NO:2.

2. A method of screening for a compound that decreases androgen receptor-mediated transactivation, the method comprising
   contacting the polypeptide of claim 1 with a protein complex including an androgen receptor, in the presence of a candidate compound;
   measuring the extent of binding between the polypeptide and the protein complex; and
   determining whether the extent of binding is less than the extent of binding between the polypeptide and the protein complex in the absence of the candidate compound, wherein an extent of binding in the presence of the compound less than the extent of binding in the absence of the compound indicates that the candidate compound decreases androgen receptor-mediated transactivation.

3. The method of claim 2, wherein the candidate compound is a peptide, a peptidomimetic, a peptoid, or a small molecule.

4. The method of claim 3, wherein the peptide is an oligopeptide or a polypeptide.

5. The method of claim 3, wherein the polypeptide and the protein complex are in a cultured cell.

6. The method of claim 5, wherein the cell is a cultured mammalian cell.

7. The method of claim 6, wherein the cultured cell is a human cell.

8. The method of claim 7, wherein the candidate compound is a peptide, a peptidomimetic, a peptoid, or a small molecule.

9. The method of claim 8, wherein the peptide is an oligopeptide or a polypeptide.

* * * * *

SEQUENCE LISTING

<160> NUMBER OF SEQ ID NOS: 17

<210> SEQ ID NO 1

<211> LENGTH: 2580
<212> TYPE: DNA
<213> ORGANISM: Homo sapiens

<400> SEQUENCE: 1

| | |
|---|---|
| atgtctcggg gtggctccta cccacacctg ttgtgggacg tgaggaaaag gtccctcggg | 60 |
| ctggaggacc cgtcccggct gcggagtcgc tacctgggaa gaagagaatt tatccaaaga | 120 |
| ttaaaacttg aagcaaccct taatgtgcat gatggttgtg ttaatacaat ctgttggaat | 180 |
| gacactggag aatatatttt atctggctca gatgacacca aattagtaat tagtaatcct | 240 |
| tacagcagaa aggttttgac aacaattcgt tcagggcacc gagcaaacat atttagtgca | 300 |
| aagttcttac cttgtacaaa tgataaacag attgtatcct gctctggaga tggagtaata | 360 |
| ttttatacca acgttgagca agatgcagaa accaacagac aatgccaatt tacgtgtcat | 420 |
| tatggaacta cttatgagat tatgactgta cccaatgacc cttacacttt tctctcttgt | 480 |
| ggtgaagatg gaactgttag gtggtttgat acacgcatca aaactagctg cacaaaagaa | 540 |
| gattgtaaag atgatatttt aattaactgt cgacgtgctg ccacgtctgt tgctatttgc | 600 |
| ccaccaatac catattacct tgctgttggt tgttctgaca gctcagtacg aatatatgat | 660 |
| cggcgaatgc tgggcacaag agctacaggg aattatgcag gtcgagggac tactggaatg | 720 |
| gttgcccgtt ttattccttc ccatcttaat aataagtcct gcagagtgac atctctgtgt | 780 |
| tacagtgaag atggtcaaga gattctcgtt agttactctt cagattacat atatcttttt | 840 |
| gacccgaaag atgatacagc acgagaactt aaaactcctt ctgcggaaga gagaagagaa | 900 |
| gagttgcgac aaccaccagt taagcgtttg agacttcgtg gtgattggtc agatactgga | 960 |
| cccagagcaa ggccggagag tgaacgagaa cgagatggag agcagagtcc aatgtgtca | 1020 |
| ttgatgcaga gaatgtctga tatgttatca agatggtttg aagaagcaag tgaggttgca | 1080 |
| caaagcaata gaggacgagg aagatctcga cccagaggtg aacaagtca atcagatatt | 1140 |
| tcaactcttc ctacggtccc atcaagtcct gatttggaag tgagtgaaac tgcaatggaa | 1200 |
| gtagatactc cagctgaaca atttcttcag ccttctacat cctctacaat gtcagctcag | 1260 |
| gctcattcga catcatctcc cacagaaagc cctcattcta ctcctttgct atcttctcca | 1320 |
| gacagtgaac aaaggcagtc tgttgaggca tctggacacc acacacatca tcagtctgat | 1380 |
| aacaataatg aaaagctgag ccccaaacca gggacaggtg aaccagtttt aagtttgcac | 1440 |
| tacagcacag aaggaacaac tacaagcaca ataaaactga actttacaga tgaatggagc | 1500 |
| agtatagcat caagttctag aggaattggg agccattgca atctgagggt caggaggaa | 1560 |
| tctttcgtcc cacagagctc agtgcaacca ccagaaggag acagtgaaac aaaagctcct | 1620 |
| gaagaatcat cagaggatgt gacaaaatat caggaaggag tatctgcaga aacccagtt | 1680 |
| gagaaccata tcaatataac acaatcagat aagttcacag ccaagccatt ggattccaac | 1740 |
| tcaggagaaa gaaatgacct caatcttgat cgctcttgtg gggttccaga gaatctgct | 1800 |
| tcatctgaaa agccaagga accagaaact tcagatcaga ctagcactga gagtgctacc | 1860 |
| aatgaaaata caccaatcc tgagcctcag ttccaaacag aagccactgg gccttcagct | 1920 |
| catgaagaaa catccaccag ggactctgct cttcaggaca cagatgacag tgatgatgac | 1980 |
| ccagtcctga tccaggtgc aagtatcga gcaggacctg tgatagacg ctctgctgtt | 2040 |
| gcccgtattc aggagttctt cagacggaga aagaaagga agaaatgga agaattggat | 2100 |
| actttgaaca ttgaaggcc gctagtaaaa atggtttata aaggccatcg caactccagg | 2160 |
| acaatgataa agaagccaa tttctggggt gctaactttg taatgagtgg ttctgactgt | 2220 |

-continued

```
ggccacattt tcatctggga tcggcacact gctgagcatt tgatgcttct ggaagctgat      2280
aatcatgtgg taaactgcct gcagccacat ccgtttgacc caatttttagc ctcatctggc     2340 atagattatg acataaagat ctggtcacca ttagaagagt caaggatttt taaccgaaaa      2400
cttgctgatg aagttataac tcgaaacgaa ctcatgctgg aagaaactag aaacaccatt      2460
acagttccag cctctttcat gttgaggatg ttggcttcac ttaatcatat ccgagctgac      2520
cggttggagg gtgacagatc agaaggctct ggtcaagaga atgaaaatga ggatgaggaa      2580
```

<210> SEQ ID NO 2
<211> LENGTH: 860
<212> TYPE: PRT
<213> ORGANISM: Homo sapiens

<400> SEQUENCE: 2

```
Met Ser Arg Gly Gly Ser Tyr Pro His Leu Leu Trp Asp Val Arg Lys
 1               5                  10                  15

Arg Ser Leu Gly Leu Glu Asp Pro Ser Arg Leu Arg Ser Arg Tyr Leu
            20                  25                  30

Gly Arg Arg Glu Phe Ile Gln Arg Leu Lys Leu Glu Ala Thr Leu Asn
        35                  40                  45

Val His Asp Gly Cys Val Asn Thr Ile Cys Trp Asn Asp Thr Gly Glu
    50                  55                  60

Tyr Ile Leu Ser Gly Ser Asp Asp Thr Lys Leu Val Ile Ser Asn Pro
65                  70                  75                  80

Tyr Ser Arg Lys Val Leu Thr Thr Ile Arg Ser Gly His Arg Ala Asn
                85                  90                  95

Ile Phe Ser Ala Lys Phe Leu Pro Cys Thr Asn Asp Lys Gln Ile Val
            100                 105                 110

Ser Cys Ser Gly Asp Gly Val Ile Phe Tyr Thr Asn Val Glu Gln Asp
        115                 120                 125

Ala Glu Thr Asn Arg Gln Cys Gln Phe Thr Cys His Tyr Gly Thr Thr
    130                 135                 140

Tyr Glu Ile Met Thr Val Pro Asn Asp Pro Tyr Thr Phe Leu Ser Cys
145                 150                 155                 160

Gly Glu Asp Gly Thr Val Arg Trp Phe Asp Thr Arg Ile Lys Thr Ser
                165                 170                 175

Cys Thr Lys Glu Asp Cys Lys Asp Asp Ile Leu Ile Asn Cys Arg Arg
            180                 185                 190

Ala Ala Thr Ser Val Ala Ile Cys Pro Pro Ile Pro Tyr Tyr Leu Ala
        195                 200                 205

Val Gly Cys Ser Asp Ser Ser Val Arg Ile Tyr Asp Arg Arg Met Leu
    210                 215                 220

Gly Thr Arg Ala Thr Gly Asn Tyr Ala Gly Arg Gly Thr Thr Gly Met
225                 230                 235                 240

Val Ala Arg Phe Ile Pro Ser His Leu Asn Asn Lys Ser Cys Arg Val
                245                 250                 255

Thr Ser Leu Cys Tyr Ser Glu Asp Gly Gln Glu Ile Leu Val Ser Tyr
            260                 265                 270

Ser Ser Asp Tyr Ile Tyr Leu Phe Asp Pro Lys Asp Asp Thr Ala Arg
        275                 280                 285

Glu Leu Lys Thr Pro Ser Ala Glu Glu Arg Arg Glu Glu Leu Arg Gln
    290                 295                 300

Pro Pro Val Lys Arg Leu Arg Leu Arg Gly Asp Trp Ser Asp Thr Gly
```

-continued

```
            305                 310                 315                 320
        Pro Arg Ala Arg Pro Glu Ser Glu Arg Glu Arg Asp Gly Glu Gln Ser
                        325                 330                 335
        Pro Asn Val Ser Leu Met Gln Arg Met Ser Asp Met Leu Ser Arg Trp
                        340                 345                 350
        Phe Glu Glu Ala Ser Glu Val Ala Gln Ser Asn Arg Gly Arg Gly Arg
                        355                 360                 365
        Ser Arg Pro Arg Gly Gly Thr Ser Gln Ser Asp Ile Ser Thr Leu Pro
                        370                 375                 380
        Thr Val Pro Ser Ser Pro Asp Leu Glu Val Ser Glu Thr Ala Met Glu
        385                 390                 395                 400
        Val Asp Thr Pro Ala Glu Gln Phe Leu Gln Pro Ser Thr Ser Ser Thr
                        405                 410                 415
        Met Ser Ala Gln Ala His Ser Thr Ser Ser Pro Thr Glu Ser Pro His
                        420                 425                 430
        Ser Thr Pro Leu Leu Ser Ser Pro Asp Ser Glu Gln Arg Gln Ser Val
                        435                 440                 445
        Glu Ala Ser Gly His His Thr His His Gln Ser Asp Asn Asn Asn Glu
        450                 455                 460
        Lys Leu Ser Pro Lys Pro Gly Thr Gly Glu Pro Val Leu Ser Leu His
        465                 470                 475                 480
        Tyr Ser Thr Glu Gly Thr Thr Thr Ser Thr Ile Lys Leu Asn Phe Thr
                        485                 490                 495
        Asp Glu Trp Ser Ser Ile Ala Ser Ser Arg Gly Ile Gly Ser His
                        500                 505                 510
        Cys Lys Ser Glu Gly Gln Glu Glu Ser Phe Val Pro Gln Ser Ser Val
                        515                 520                 525
        Gln Pro Pro Glu Gly Asp Ser Glu Thr Lys Ala Pro Glu Glu Ser Ser
                        530                 535                 540
        Glu Asp Val Thr Lys Tyr Gln Glu Gly Val Ser Ala Glu Asn Pro Val
        545                 550                 555                 560
        Glu Asn His Ile Asn Ile Thr Gln Ser Asp Lys Phe Thr Ala Lys Pro
                        565                 570                 575
        Leu Asp Ser Asn Ser Gly Glu Arg Asn Asp Leu Asn Leu Asp Arg Ser
                        580                 585                 590
        Cys Gly Val Pro Glu Glu Ser Ala Ser Glu Lys Ala Lys Glu Pro
                        595                 600                 605
        Glu Thr Ser Asp Gln Thr Ser Thr Glu Ser Ala Thr Asn Glu Asn Asn
                        610                 615                 620
        Thr Asn Pro Glu Pro Gln Phe Gln Thr Glu Ala Thr Gly Pro Ser Ala
        625                 630                 635                 640
        His Glu Glu Thr Ser Thr Arg Asp Ser Ala Leu Gln Asp Thr Asp Asp
                        645                 650                 655
        Ser Asp Asp Asp Pro Val Leu Ile Pro Gly Ala Arg Tyr Arg Ala Gly
                        660                 665                 670
        Pro Gly Asp Arg Arg Ser Ala Val Ala Arg Ile Gln Glu Phe Phe Arg
                        675                 680                 685
        Arg Arg Lys Glu Arg Lys Glu Met Glu Glu Leu Asp Thr Leu Asn Ile
                        690                 695                 700
        Arg Arg Pro Leu Val Lys Met Val Tyr Lys Gly His Arg Asn Ser Arg
        705                 710                 715                 720
        Thr Met Ile Lys Glu Ala Asn Phe Trp Gly Ala Asn Phe Val Met Ser
                        725                 730                 735
```

```
Gly Ser Asp Cys Gly His Ile Phe Ile Trp Asp Arg His Thr Ala Glu
            740                 745                 750

His Leu Met Leu Leu Glu Ala Asp Asn His Val Val Asn Cys Leu Gln
            755                 760                 765

Pro His Pro Phe Asp Pro Ile Leu Ala Ser Ser Gly Ile Asp Tyr Asp
            770                 775                 780

Ile Lys Ile Trp Ser Pro Leu Glu Glu Ser Arg Ile Phe Asn Arg Lys
785                 790                 795                 800

Leu Ala Asp Glu Val Ile Thr Arg Asn Glu Leu Met Leu Glu Thr
                805                 810                 815

Arg Asn Thr Ile Thr Val Pro Ala Ser Phe Met Leu Arg Met Leu Ala
            820                 825                 830

Ser Leu Asn His Ile Arg Ala Asp Arg Leu Glu Gly Asp Arg Ser Glu
            835                 840                 845

Gly Ser Gly Gln Glu Asn Glu Asn Glu Asp Glu Glu
            850                 855                 860

<210> SEQ ID NO 3
<211> LENGTH: 3016
<212> TYPE: DNA
<213> ORGANISM: Homo sapiens
<220> FEATURE:
<221> NAME/KEY: CDS
<222> LOCATION: (18)...(2597)

<400> SEQUENCE: 3
```

| | | | | | | | | | | | | | | | | |
|---|---|---|---|---|---|---|---|---|---|---|---|---|---|---|---|---|
| ccggctcagg cagagcc | atg | tct | cgg | ggt | ggc | tcc | tac | cca | cac | ctg | ttg | | | | | 50 |
| | Met | Ser | Arg | Gly | Gly | Ser | Tyr | Pro | His | Leu | Leu | | | | | |
| | 1 | | | 5 | | | | | | 10 | | | | | | |

```
tgg gac gtg agg aaa agg tcc ctc ggg ctg gag gac ccg tcc cgg ctg       98
Trp Asp Val Arg Lys Arg Ser Leu Gly Leu Glu Asp Pro Ser Arg Leu
            15                  20                  25 cgg agt cgc tac ctg gga aga aga gaa ttt atc caa aga tta aaa ctt      146
Arg Ser Arg Tyr Leu Gly Arg Arg Glu Phe Ile Gln Arg Leu Lys Leu
        30                  35                  40 gaa gca acc ctt aat gtg cat gat ggt tgt gtt aat aca atc tgt tgg      194
Glu Ala Thr Leu Asn Val His Asp Gly Cys Val Asn Thr Ile Cys Trp
    45                  50                  55 aat gac act gga gaa tat att tta tct ggc tca gat gac acc aaa tta      242
Asn Asp Thr Gly Glu Tyr Ile Leu Ser Gly Ser Asp Asp Thr Lys Leu
60                  65                  70                  75 gta att agt aat cct tac agc aga aag gtt ttg aca aca att cgt tca      290
Val Ile Ser Asn Pro Tyr Ser Arg Lys Val Leu Thr Thr Ile Arg Ser
                80                  85                  90 ggg cac cga gca aac ata ttt agt gca aag ttc tta cct tgt aca aat      338
Gly His Arg Ala Asn Ile Phe Ser Ala Lys Phe Leu Pro Cys Thr Asn
            95                 100                 105 gat aaa cag att gta tcc tgc tct gga gat gga gta ata ttt tat acc      386
Asp Lys Gln Ile Val Ser Cys Ser Gly Asp Gly Val Ile Phe Tyr Thr
        110                 115                 120 aac gtt gag caa gat gca gaa acc aac aga caa tgc caa ttt acg tgt      434
Asn Val Glu Gln Asp Ala Glu Thr Asn Arg Gln Cys Gln Phe Thr Cys
    125                 130                 135 cat tat gga act act tat gag att atg act gta ccc aat gac cct tac      482
His Tyr Gly Thr Thr Tyr Glu Ile Met Thr Val Pro Asn Asp Pro Tyr
140                 145                 150                 155 act ttt ctc tct tgt ggt gaa gat gga act gtt agg tgg ttt gat aca      530
Thr Phe Leu Ser Cys Gly Glu Asp Gly Thr Val Arg Trp Phe Asp Thr
                160                 165                 170
```

-continued

```
cgc atc aaa act agc tgc aca aaa gaa gat tgt aaa gat gat att tta      578
Arg Ile Lys Thr Ser Cys Thr Lys Glu Asp Cys Lys Asp Asp Ile Leu
        175                 180                 185 att aac tgt cga cgt gct gcc acg tct gtt gct att tgc cca cca ata      626
Ile Asn Cys Arg Arg Ala Ala Thr Ser Val Ala Ile Cys Pro Pro Ile
190                 195                 200 cca tat tac ctt gct gtt ggt tgt tct gac agc tca gta cga ata tat      674
Pro Tyr Tyr Leu Ala Val Gly Cys Ser Asp Ser Ser Val Arg Ile Tyr
    205                 210                 215 gat cgg cga atg ctg ggc aca aga gct aca ggg aat tat gca ggt cga      722
Asp Arg Arg Met Leu Gly Thr Arg Ala Thr Gly Asn Tyr Ala Gly Arg
220                 225                 230                 235 ggg act act gga atg gtt gcc cgt ttt att cct tcc cat ctt aat aat      770
Gly Thr Thr Gly Met Val Ala Arg Phe Ile Pro Ser His Leu Asn Asn
            240                 245                 250 aag tcc tgc aga gtg aca tct ctg tgt tac agt gaa gat ggt caa gag      818
Lys Ser Cys Arg Val Thr Ser Leu Cys Tyr Ser Glu Asp Gly Gln Glu
        255                 260                 265 att ctc gtt agt tac tct tca gat tac ata tat ctt ttt gac ccg aaa      866
Ile Leu Val Ser Tyr Ser Ser Asp Tyr Ile Tyr Leu Phe Asp Pro Lys
    270                 275                 280 gat gat aca gca cga gaa ctt aaa act cct tct gcg gaa gag aga aga      914
Asp Asp Thr Ala Arg Glu Leu Lys Thr Pro Ser Ala Glu Glu Arg Arg
285                 290                 295 gaa gag ttg cga caa cca cca gtt aag cgt ttg aga ctt cgt ggt gat      962
Glu Glu Leu Arg Gln Pro Pro Val Lys Arg Leu Arg Leu Arg Gly Asp
300                 305                 310                 315 tgg tca gat act gga ccc aga gca agg ccg gag agt gaa cga gaa cga     1010
Trp Ser Asp Thr Gly Pro Arg Ala Arg Pro Glu Ser Glu Arg Glu Arg
            320                 325                 330 gat gga gag cag agt ccc aat gtg tca ttg atg cag aga atg tct gat     1058
Asp Gly Glu Gln Ser Pro Asn Val Ser Leu Met Gln Arg Met Ser Asp
        335                 340                 345 atg tta tca aga tgg ttt gaa gaa gca agt gag gtt gca caa agc aat     1106
Met Leu Ser Arg Trp Phe Glu Glu Ala Ser Glu Val Ala Gln Ser Asn
    350                 355                 360 aga gga cga gga aga tct cga ccc aga ggt gga aca agt caa tca gat     1154
Arg Gly Arg Gly Arg Ser Arg Pro Arg Gly Gly Thr Ser Gln Ser Asp
365                 370                 375 att tca act ctt cct acg gtc cca tca agt cct gat ttg gaa gtg agt     1202
Ile Ser Thr Leu Pro Thr Val Pro Ser Ser Pro Asp Leu Glu Val Ser
380                 385                 390                 395 gaa act gca atg gaa gta gat act cca gct gaa caa ttt ctt cag cct     1250
Glu Thr Ala Met Glu Val Asp Thr Pro Ala Glu Gln Phe Leu Gln Pro
            400                 405                 410 tct aca tcc tct aca atg tca gct cag gct cat tcg aca tca tct ccc     1298
Ser Thr Ser Ser Thr Met Ser Ala Gln Ala His Ser Thr Ser Ser Pro
        415                 420                 425 aca gaa agc cct cat tct act cct ttg cta tct tct cca gac agt gaa     1346
Thr Glu Ser Pro His Ser Thr Pro Leu Leu Ser Ser Pro Asp Ser Glu
    430                 435                 440 caa agg cag tct gtt gag gca tct gga cac cac aca cat cat cag tct     1394
Gln Arg Gln Ser Val Glu Ala Ser Gly His His Thr His His Gln Ser
445                 450                 455 gat aac aat aat gaa aag ctg agc ccc aaa cca ggg aca ggt gaa cca     1442
Asp Asn Asn Asn Glu Lys Leu Ser Pro Lys Pro Gly Thr Gly Glu Pro
460                 465                 470                 475 gtt tta agt ttg cac tac agc aca gaa gga aca act aca agc aca ata     1490
Val Leu Ser Leu His Tyr Ser Thr Glu Gly Thr Thr Thr Ser Thr Ile
```

```
                  480             485             490
aaa ctg aac ttt aca gat gaa tgg agc agt ata gca tca agt tct aga        1538
Lys Leu Asn Phe Thr Asp Glu Trp Ser Ser Ile Ala Ser Ser Ser Arg
            495             500             505 gga att ggg agc cat tgc aaa tct gag ggt cag gag gaa tct ttc gtc        1586
Gly Ile Gly Ser His Cys Lys Ser Glu Gly Gln Glu Glu Ser Phe Val
        510             515             520 cca cag agc tca gtg caa cca cca gaa gga gac agt gaa aca aaa gct        1634
Pro Gln Ser Ser Val Gln Pro Pro Glu Gly Asp Ser Glu Thr Lys Ala
    525             530             535 cct gaa gaa tca tca gag gat gtg aca aaa tat cag gaa gga gta tct        1682
Pro Glu Glu Ser Ser Glu Asp Val Thr Lys Tyr Gln Glu Gly Val Ser
540             545             550             555 gca gaa aac cca gtt gag aac cat atc aat ata aca caa tca gat aag        1730
Ala Glu Asn Pro Val Glu Asn His Ile Asn Ile Thr Gln Ser Asp Lys
            560             565             570 ttc aca gcc aag cca ttg gat tcc aac tca gga gaa aga aat gac ctc        1778
Phe Thr Ala Lys Pro Leu Asp Ser Asn Ser Gly Glu Arg Asn Asp Leu
        575             580             585 aat ctt gat cgc tct tgt ggg gtt cca gaa gaa tct gct tca tct gaa        1826
Asn Leu Asp Arg Ser Cys Gly Val Pro Glu Glu Ser Ala Ser Ser Glu
    590             595             600 aaa gcc aag gaa cca gaa act tca gat cag act agc act gag agt gct        1874
Lys Ala Lys Glu Pro Glu Thr Ser Asp Gln Thr Ser Thr Glu Ser Ala
605             610             615 acc aat gaa aat aac acc aat cct gag cct cag ttc caa aca gaa gcc        1922
Thr Asn Glu Asn Asn Thr Asn Pro Glu Pro Gln Phe Gln Thr Glu Ala
620             625             630             635 act ggg cct tca gct cat gaa gaa aca tcc acc agg gac tct gct ctt        1970
Thr Gly Pro Ser Ala His Glu Glu Thr Ser Thr Arg Asp Ser Ala Leu
            640             645             650 cag gac aca gat gac agt gat gat gac cca gtc ctg atc cca ggt gca        2018
Gln Asp Thr Asp Asp Ser Asp Asp Asp Pro Val Leu Ile Pro Gly Ala
        655             660             665 agg tat cga gca gga cct ggt gat aga cgc tct gct gtt gcc cgt att        2066
Arg Tyr Arg Ala Gly Pro Gly Asp Arg Arg Ser Ala Val Ala Arg Ile
    670             675             680 cag gag ttc ttc aga cgg aga aaa gaa agg aaa gaa atg gaa gaa ttg        2114
Gln Glu Phe Phe Arg Arg Arg Lys Glu Arg Lys Glu Met Glu Glu Leu
685             690             695 gat act ttg aac att aga agg ccg cta gta aaa atg gtt tat aaa ggc        2162
Asp Thr Leu Asn Ile Arg Arg Pro Leu Val Lys Met Val Tyr Lys Gly
700             705             710             715 cat cgc aac tcc agg aca atg ata aaa gaa gcc aat ttc tgg ggt gct        2210
His Arg Asn Ser Arg Thr Met Ile Lys Glu Ala Asn Phe Trp Gly Ala
            720             725             730 aac ttt gta atg agt ggt tct gac tgt ggc cac att ttc atc tgg gat        2258
Asn Phe Val Met Ser Gly Ser Asp Cys Gly His Ile Phe Ile Trp Asp
        735             740             745 cgg cac act gct gag cat ttg atg ctt ctg gaa gct gat aat cat gtg        2306
Arg His Thr Ala Glu His Leu Met Leu Leu Glu Ala Asp Asn His Val
    750             755             760 gta aac tgc ctg cag cca cat ccg ttt gac cca att tta gcc tca tct        2354
Val Asn Cys Leu Gln Pro His Pro Phe Asp Pro Ile Leu Ala Ser Ser
765             770             775 ggc ata gat tat gac ata aag atc tgg tca cca tta gaa gag tca agg        2402
Gly Ile Asp Tyr Asp Ile Lys Ile Trp Ser Pro Leu Glu Glu Ser Arg
780             785             790             795 att ttt aac cga aaa ctt gct gat gaa gtt ata act cga aac gaa ctc        2450
```

-continued

```
Ile Phe Asn Arg Lys Leu Ala Asp Glu Val Ile Thr Arg Asn Glu Leu
            800                 805                 810
atg ctg gaa gaa act aga aac acc att aca gtt cca gcc tct ttc atg    2498
Met Leu Glu Glu Thr Arg Asn Thr Ile Thr Val Pro Ala Ser Phe Met
        815                 820                 825 ttg agg atg ttg gct tca ctt aat cat atc cga gct gac cgg ttg gag    2546
Leu Arg Met Leu Ala Ser Leu Asn His Ile Arg Ala Asp Arg Leu Glu
        830                 835                 840 ggt gac aga tca gaa ggc tct ggt caa gag aat gaa aat gag gat gag    2594
Gly Asp Arg Ser Glu Gly Ser Gly Gln Glu Asn Glu Asn Glu Asp Glu
    845                 850                 855 gaa taataaactc tttttggcaa gcacttaaat gttctgaaat ttgtataaga         2647
Glu
860 catttattat atttttttct ttacagagct ttagtgcaat tttaaggtta tggttttttgg  2707 agttttttccc ttttttttggg ataacctaac attggtttgg aatgattgtg tgcatgaatt  2767 tgggagattg tataaaacaa aactagcaga atgttttttaa aactttttgc cgtgtatgag  2827 gagtgctaga aaatgcaaag tgcaatattt tccctaacct tcaaatgtgg gagcttggat  2887 caatgttgaa gaataatttt catcatagtg aaaatgttgg ttcaaataaa tttctacact  2947 tgccatttgc atgtttgttg ctttctaatt aaagaaactg gttgttttaa aaaaaaaaa   3007 aaggaattc                                                          3016

<210> SEQ ID NO 4
<211> LENGTH: 20
<212> TYPE: DNA
<213> ORGANISM: Artificial Sequence
<220> FEATURE:
<223> OTHER INFORMATION: primer for PCR

<400> SEQUENCE: 4
ggaacatttt ggcaaagaca                                                20

<210> SEQ ID NO 5
<211> LENGTH: 20
<212> TYPE: DNA
<213> ORGANISM: Artificial Sequence
<220> FEATURE:
<223> OTHER INFORMATION: primer for PCR

<400> SEQUENCE: 5
attcatgatc ttygcgatgc                                                20

<210> SEQ ID NO 6
<211> LENGTH: 8
<212> TYPE: PRT
<213> ORGANISM: Artificial Sequence
<220> FEATURE:
<223> OTHER INFORMATION: motif

<400> SEQUENCE: 6

Asp Tyr Ser Thr Gly Tyr His Tyr
 1               5

<210> SEQ ID NO 7
<211> LENGTH: 7
<212> TYPE: PRT
<213> ORGANISM: Artificial Sequence
<220> FEATURE:
<221> NAME/KEY: VARIANT
<222> LOCATION: (1)...(7)
<223> OTHER INFORMATION: Xaa = Any Amino Acid
```

```
<220> FEATURE:
<223> OTHER INFORMATION: motif

<400> SEQUENCE: 7

Cys Lys Xaa Phe Phe Lys Arg
 1               5

<210> SEQ ID NO 8
<211> LENGTH: 9
<212> TYPE: PRT
<213> ORGANISM: Artificial Sequence
<220> FEATURE:
<221> NAME/KEY: VARIANT
<222> LOCATION: (1)...(9)
<223> OTHER INFORMATION: Xaa = Any Amino Acid
<220> FEATURE:
<223> OTHER INFORMATION: motif

<400> SEQUENCE: 8

Cys Pro Ala Cys Arg Phe Xaa Lys Cys
 1               5

<210> SEQ ID NO 9
<211> LENGTH: 16
<212> TYPE: DNA
<213> ORGANISM: Homo sapiens

<400> SEQUENCE: 9
tgggtacatt ttgttc                                              16

<210> SEQ ID NO 10
<211> LENGTH: 16
<212> TYPE: DNA
<213> ORGANISM: Artificial Sequence
<220> FEATURE:
<223> OTHER INFORMATION: mutated nucleic acid sequence

<400> SEQUENCE: 10
tgggtaggtt ttgctc                                              16

<210> SEQ ID NO 11
<211> LENGTH: 27
<212> TYPE: DNA
<213> ORGANISM: Artificial Sequence
<220> FEATURE:
<223> OTHER INFORMATION: degenerate primer
<220> FEATURE:
<221> NAME/KEY: misc_feature
<222> LOCATION: 7-10, 13, 19
<223> OTHER INFORMATION: n = inosine
<220> FEATURE:
<221> NAME/KEY: misc_feature
<222> LOCATION: 22
<223> OTHER INFORMATION: n = A, T, G, or C

<400> SEQUENCE: 11
rcayttnnnn arnckrcank mnkgrca                                  27

<210> SEQ ID NO 12
<211> LENGTH: 22
<212> TYPE: DNA
<213> ORGANISM: Artificial Sequence
<220> FEATURE:
<223> OTHER INFORMATION: degenerate primer
<220> FEATURE:
<221> NAME/KEY: misc_feature
<222> LOCATION: 9, 12, 15, 18
<223> OTHER INFORMATION: n = inosine
```

```
<400> SEQUENCE: 12
gayrarkcnw cnggnwrnca yt                                    22

<210> SEQ ID NO 13
<211> LENGTH: 20
<212> TYPE: DNA
<213> ORGANISM: Artificial Sequence
<220> FEATURE:
<223> OTHER INFORMATION: synthetically generated primer

<400> SEQUENCE: 13
tctggtggtt gcactgagct                                       20

<210> SEQ ID NO 14
<211> LENGTH: 19
<212> TYPE: DNA
<213> ORGANISM: Artificial Sequence
<220> FEATURE:
<223> OTHER INFORMATION: synthetically generated primer

<400> SEQUENCE: 14
acaatgtcag ctcaggctc                                        19

<210> SEQ ID NO 15
<211> LENGTH: 57
<212> TYPE: DNA
<213> ORGANISM: Artificial Sequence
<220> FEATURE:
<223> OTHER INFORMATION: synthetically generated primer
<220> FEATURE:
<221> NAME/KEY: misc_feature
<222> LOCATION: (1)...(57)
<223> OTHER INFORMATION: n = A,T,C or G

<400> SEQUENCE: 15
aagcagtggt aacaacgcag agtactttttt tttttttttt tttttttttt tttttnn    57

<210> SEQ ID NO 16
<211> LENGTH: 27
<212> TYPE: DNA
<213> ORGANISM: Artificial Sequence
<220> FEATURE:
<221> NAME/KEY: misc_feature
<222> LOCATION: (1)...(27)
<223> OTHER INFORMATION: n = A,T,C or G
<220> FEATURE:
<223> OTHER INFORMATION: synthetically generated primer

<400> SEQUENCE: 16
tttttttttt tttttttttt tttttnn                               27

<210> SEQ ID NO 17
<211> LENGTH: 30
<212> TYPE: DNA
<213> ORGANISM: Artificial Sequence
<220> FEATURE:
<223> OTHER INFORMATION: synthetically generated primer

<400> SEQUENCE: 17
aagcagtggt aacaacgcag agtacgcggg                            30
```